(12) United States Patent
Kalem et al.

(10) Patent No.: US 11,696,884 B2
(45) Date of Patent: Jul. 11, 2023

(54) COMPOSITIONS COMPRISING MENTHOL COMPOUNDS AS SMOOTHING AGENTS

(71) Applicant: Symrise AG, Holzminden (DE)

(72) Inventors: Cécile Kalem, Issy-les-Moulineaux (FR); Dominik Stuhlmann, Holzminden (DE); Aurélie Trunet, Levallois Perret (FR); Denis Brouard, Saint Ouen (FR)

(73) Assignee: Symrise AG, Holzminden (DE)

( * ) Notice: Subject to any disclaimer, the term of this patent is extended or adjusted under 35 U.S.C. 154(b) by 303 days.

(21) Appl. No.: 15/554,791

(22) PCT Filed: Feb. 17, 2016

(86) PCT No.: PCT/EP2016/053394
§ 371 (c)(1),
(2) Date: Aug. 31, 2017

(87) PCT Pub. No.: WO2016/139066
PCT Pub. Date: Sep. 9, 2016

(65) Prior Publication Data
US 2018/0042832 A1 Feb. 15, 2018

(30) Foreign Application Priority Data

Mar. 4, 2015 (EP) .................................... 15157677

(51) Int. Cl.
| | | |
|---|---|---|
| *A61K 8/49* | (2006.01) | |
| *A61Q 19/00* | (2006.01) | |
| *A61K 8/42* | (2006.01) | |
| *A61K 8/37* | (2006.01) | |
| *A61K 8/34* | (2006.01) | |
| *A61Q 5/10* | (2006.01) | |
| *A61Q 5/04* | (2006.01) | |
| *A61Q 5/08* | (2006.01) | |
| *A61Q 5/12* | (2006.01) | |

(52) U.S. Cl.
CPC ................ *A61K 8/498* (2013.01); *A61K 8/34* (2013.01); *A61K 8/345* (2013.01); *A61K 8/37* (2013.01); *A61K 8/375* (2013.01); *A61K 8/42* (2013.01); *A61K 8/4973* (2013.01); *A61Q 5/04* (2013.01); *A61Q 5/08* (2013.01); *A61Q 5/10* (2013.01); *A61Q 5/12* (2013.01); *A61Q 19/005* (2013.01); *A61K 2800/244* (2013.01)

(58) Field of Classification Search
CPC ................................ A61Q 5/10; A61K 36/534
See application file for complete search history.

(56) References Cited

U.S. PATENT DOCUMENTS

| 4,357,141 | A  * | 11/1982 | Grollier | A61K 8/84 |
|---|---|---|---|---|
| | | | | 424/DIG. 2 |
| 7,179,301 | B2 * | 2/2007 | Vidal | A61Q 5/10 |
| | | | | 8/405 |
| 2008/0253976 | A1 * | 10/2008 | Scott | A61K 8/0216 |
| | | | | 424/49 |
| 2010/0150854 | A1 * | 6/2010 | Schmaus | A61K 8/06 |
| | | | | 424/59 |
| 2013/0195773 | A1 * | 8/2013 | Kindel | A23L 1/22075 |
| | | | | 424/49 |
| 2014/0171355 | A1 * | 6/2014 | Bellon | A61Q 13/00 |
| | | | | 512/2 |
| 2016/0008297 | A1 * | 1/2016 | Schmaus | A61K 9/0014 |
| | | | | 424/48 |

FOREIGN PATENT DOCUMENTS

| EP | 80 148 A1 | 6/1983 |
|---|---|---|
| EP | 507 190 A1 | 10/1992 |
| EP | 1 332 772 A2 | 8/2003 |
| EP | 2 620 137 A1 | 7/2013 |
| WO | 2014/023640 A2 | 2/2014 |

* cited by examiner

*Primary Examiner* — Kyle A Purdy
(74) *Attorney, Agent, or Firm* — Dilworth & Barrese, LLP

(57) ABSTRACT

The present invention relates to a soothing composition, comprising (a) menthol compounds, and (b) one or more cosmetically acceptable carriers.

3 Claims, No Drawings

COMPOSITIONS COMPRISING MENTHOL COMPOUNDS AS SMOOTHING AGENTS

FIELD OF INVENTION

The present invention belongs to the topical cosmetic and the pharmaceutical area and relates to a soothing composition comprising menthol compounds of formula (Ia) and/or (Ib), which can effectively reduce the skin and scalp irritation sensation, especially during hair treatment, such as during hair colouring process.

The invention further relates to cosmetic formulations, especially hair treatment formulations, more especially hair colouring formulations comprising the mentioned soothing ingredient composition as well as the methods of hair treatment, especially hair colouring.

STATE OF THE ART

Recent years hair colouring has become immensely popular and globally hair colorants are a rapidly growing industry. As a result of an increasingly aging and thus greying global population, demand for hair dye products has been increasing rapidly, a trend likely to continue into the future.

There are a variety of reasons of hair colouring, including covering or hiding of grey hair, to change to a colour regarded as more fashionable or desirable, or to restore the original hair colour after it has been discoloured by hairdressing processes or sun bleaching.

Modern commercial hair colouring products can be divided into 2 main categories according to the chemistry involved:

Hair dye products with Oxidative process which may be further divided into 3 subcategories:

(i-i) permanent hair dyes (representing 70% of the market) are generally marketed as a two component kit containing a colouring cream and a revealing cream. The colouring cream contains the dye precursors (oxidation base and a coupler) and an alkali (usually ammonia or monoethanolamine). The revealing cream is the oxidizing agent (almost exclusively a stabilised hydrogen peroxide solution);

(i-ii) semi-permanent hair dyes (the hair is lightened less and the colours fade with time);

(i-iii) auto-oxidative hair dyes (offers the users, particularly males, colour development over a period of time);

Hair dye products with non-oxidative process (semi-permanent hair dyes).

Till now the researches focus mostly on the improvement of the colouring effect, duration, and the protection of the hair.

EP 2476405 A1 disclosed an oxidative hair colouring composition, which comprises non-ammonia alkalizing agent and can provide a lift and/or intensity of colouration.

EP 1022014 A1 published a hair dye composition comprising an acid dye and an alkylene carbonate, which can prevent the scalp from colouring and has good fastness to shampoo.

WO 2001 072271 A2 related to an alkaline hair bleaching and colouring composition, which contains at least one oxidizing agent and a buffering system. This composition has a longer shelf-life and provides good grey coverage as well as quality lightening.

U.S. Pat. No. 8,828,100 B1 concerned a colouring system comprising at least one of a metal salt to achieve the natural colour and shade.

EP 0875237 A2 disclosed a hair dye composition which improved resistance to dripping and running once applied to the hair by the addition of rheology modifiers.

Additionally, US 2003/0140430 A1 developed a stable oxidative hair dye composition comprising, besides the two essential components dye precursor as colouring agent, oxidizing agent, a non-ionic polyether polyurethane polymer and/or a cationic conditioning agent, that result in long-lasting and true colour and do not adversely affect the texture and condition of the hair after application In contrast to the enthusiasm for "better and longer" colouring effect as well as the full protection for the hair, few studies are concentrated on the relief of the cutaneous discomfort caused by the application of hair colorants. On one hand the hair colouring is an easy and popular cosmetic practice, and the consumers have many choices of varied colouring products, that can dye their hair anytime into any colour. But on the other hand the use of the varied products can also cause a range of adverse cutaneous sensation during or slightly after the hair colouration, such as itching, irritation and burning feelings. Especially for the people having "sensitive scalp", the approximate one hour-long process of hair colouring is usually not a comfortable experience.

A "sensitive scalp" is likewise characterized by reddening of the skin, tingling, prickling, and burning. Triggers are, for example shampoos or soaps, or other hair care compositions, surfactants, hard water having high lime concentrations and/or mechanical stress. Erythemas and hyperseborrhoea (excessive production of sebum) of the scalp and dandruff are often associated with the phenomena described.

Besides the hair colouring process, when certain cosmetic formulations with a pH between 6.5 and 12 are applied, scalp/skin irritation sensation is also caused, especially for populations with sensitive skins. The mentioned cosmetic formulations may include hair colouration, hair perm, soaps, hair relaxer, depilatories, and other commercial cosmetic formulations with pH value >6.5.

Hence, an object of the present invention was to find a substance to reduce the skin/scalp irritation sensation caused by these cosmetic formulations with pH >6.5, and to provide a soothing composition which can be applied to eliminate the uncomfortable cutaneous sensation to great extent and bring calming feeling on the skin and/or scalp. The uncomfortable sensation generally includes stinging, burning, tingling, tickling and skin tightness, especially the scalp irritation during the hair treatment, especially the colouration. Another object of the present invention was to provide various stable cosmetic formulations comprising the said soothing composition, which compared to the formulations of the prior art could intensively relieve the mentioned uncomfortable cutaneous sensation experienced by the consumers during their application.

DESCRIPTION OF THE INVENTION

The present invention provides a soothing composition comprising menthol compounds corresponding to the formula (Ia) and/or (Ib). The invention further provides cosmetic formulations, especially hair treatment formulations, more especially hair colouring formulations comprising the said soothing composition containing menthol compounds of formula (Ia) or (Ib) as well as the methods of hair treatment, especially hair colouring.

The present invention provides a soothing composition, comprising
(a) menthol compounds corresponding to formulas (I), (II) and/or (III)

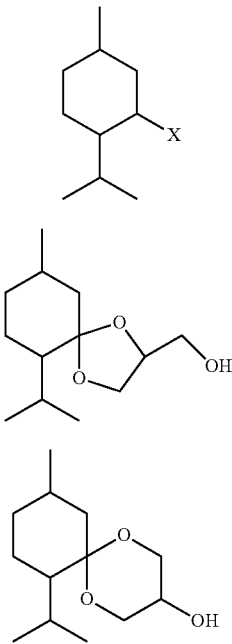

(I)

(II)

(III)

in which X represents —Y or —COZ and Y represents the following groups:
(i) a linear or branched alkyl or hydroxyl alkyl radical containing 1 to 6 carbon atoms or an allyl radical;
(ii) a hydroxy or dihydroxyalkyl radical containing 1 to 6 carbon atoms;
(iii) a radical —OCR$^1$;
(iv) a radical —OCO(M)OH;
(v) a radical —OCO—S
(vi) a radical —OC(CH$_2$)$_n$COR$^2$
wherein
M represents a linear or branched alkyl and/or alkenyl radical containing 1 to 10, preferably, 1 to 4 carbon atoms;
S represents a carbohydrate radical containing 5 to 12 carbon atoms, preferably, a fructose, a glucose or a sucrose radical;
n stands for 0 or for numbers of 1 to 6, preferably, of 2 to 3;
R$^1$ represents a linear or branched alkyl- or hydroxyl alkyl radical containing 1 to 6, preferably, 1 to 2 carbon atoms or an allyl radical;
R$^2$ represents a hydroxyl radical or a radical —NR$^3$R$^4$;
R$^3$ and R$^4$, independently of one another, represent hydrogen or a linear or branched alkyl or hydroxyl alkyl radical containing 1 to 6, preferably, 1 to 2 carbon atoms,
while Z represents the following groups:
(vii) a radical NR$^5$R$^6$ or
(viii) a radical NHR$^7$
wherein
R$^5$ and R$^6$, independently of one another, represent hydrogen or a linear or branched alkyl or hydroxyl alkyl radical containing 1 to 6, preferably, 1 to 2 carbon atoms, a phenyl radical or an alkoxyphenyl radical containing 1 to 6, preferably, 1 to 2 carbon atoms in the alkoxy radical;
R$^7$ represents a radical —(CH$_2$)$_n$COOR$^8$;
R$^8$ represents a linear or branched alkyl or hydroxy alkyl radical containing 1 to 6, preferably, 1 to 2 carbon atoms, and
n stands for 0 or for numbers of 1 to 10, preferably, of 1 to 4, and
(b) one or more cosmetically acceptable carriers.

Soothing

In the present invention the term "soothing" means relieving from skin and/or scalp discomfort, such as stinging, burning, tingling, tickling and skin tightness, during and/or after the application of cosmetic formulations, especially those with a pH between 6.5 to 12, and at the meantime bringing a calming, emollient and lenitive sensation.

The term "cooling" means making the skin fresh, giving an impression of freshness. The sensation is similar as when the skin is immersed in cold water, or when cold or ice is put on the skin. A "cooling" effect gives the sensation to lower the temperature of the skin in a pleasant way.

Menthol Compounds

Menthol compounds, which can be used within the meaning of the invention, are, for example, selected from the group consisting of menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamat, monomethyl succinate (FEMA GRAS 3810), monomethyl glutamate (FEMA GRAS 4006), menthoxy-1,2-propanediol (FEMA GRAS 3784), menthoxy-2-methyl-1,2-propandiol (FEMA GRAS 3849) and the menthan carboxylic acid esters and amides WS-3, WS-4, WS-5, WS-12, WS-14 and WS-30 and mixtures thereof.

[1]FEMA stands for "Flavor and Extracts Manufacturers Association" and GRAS is defined as "Generally Regarded As Safe". A FEMA GRAS designation means that the substance designated such has been tested according to standard methods and is considered to be toxicologically safe.

Although menthol has been known as a cooling substance for many decades and is indispensible in a large number of uses to this date, this substance certainly has quite a number of disadvantages: it is volatile, has a pungent odour and a bitter flavour. In higher concentrations it is no longer percepted to be pleasantly cooling, but to be pungent and burning. Finally, menthol cannot be formulated arbitrarily, as it may interact with other chemical components. This has led to the development of the most diverse menthol compounds, of which a number within the meaning of the invention is capable to neutralize the negative features of menthofuran. All these substances are commercially available and can be produced according to the conventional methods of organic chemistry.

A first important representative of the substances forming component (b) is monomethyl succinate (FEMA GRAS 3810), which was patented as a substance already in 1963 for Brown & Williamson Tobacco Corp. (U.S. Pat. No. 3,111,127). As a cooling agent it is subject matter of U.S. Pat. Nos. 5,725,865 and 5,843,466 (V. Mane Fils). Both the succinate and also the analogue monomethyl glutarate (FEMA GRAS 4006) are important representatives of monomenthyl esters on the basis of di- and poly-carboxylic acids:

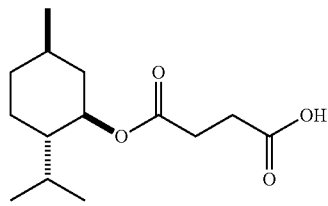

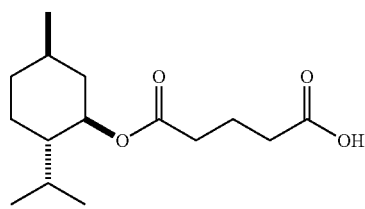

Examples of applications of these substances are available, for example, in the publications of WO 2003 043431 (Unilever) or EP 1332772 A1 (IFF).

The next important group of preferred menthol compounds within the meaning of the invention comprises carbonate esters of menthol and polyols such as, for example, glycols, glycerol or carbohydrates such as, for example, menthol ethylenglycol carbonate (FEMA GRAS 3805=Frescolat® MGC), menthol propylenglycol carbonate (FEMA GRAS 3784=Frescolat® MPC), menthol 2-methyl-1,2-propandiol carbonate (FEMA GRAS 3849) or the corresponding sugar derivatives:

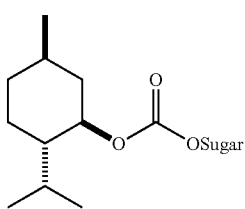

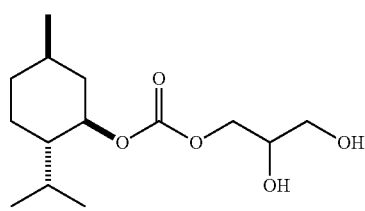

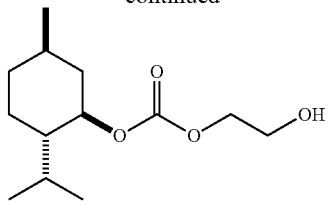

Menthol ethylene glycol carbonate

The use of such substances as a cooling agent for cigarettes is, for example, subject of U.S. Pat. No. 3,419,543 (Mold et al.) of 1968; their use as a physiological cooling agent is claimed in DE 4226043 A1 (H&R).

The menthol compounds menthyl lactate (FEMA GRAS 3748=Frescolat® ML) and, particularly, menthone glyceryl acetal (FEMA GRAS 3807) or, respectively, menthone glyceryl ketal (FEMA GRAS 3808), which is marketed under the trade name Frescolat® MAG are preferred within the meaning of the invention.

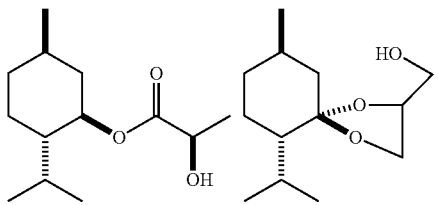

The first structure is obtained by esterification of lactic acid with menthol, the latter by acetalisation of menthone with glycerol (cf. DE 2608226 A1, H&R). This group of compounds also includes 3-(I-Menthoxy)-1,2,propandiol, which is also known as Cooling Agent 10 (FEMA GRAS 3784, cf. U.S. Pat. No. 6,328,982, TIC), and 3-(I-Menthoxy)-2-methyl-1,2,propandiol (FEMA GRAS 3849), which contains an additional methyl group.

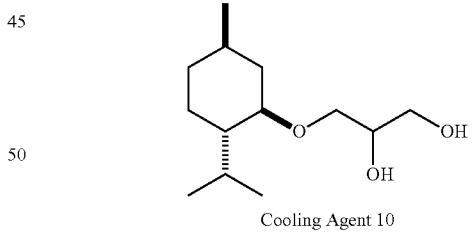

Cooling Agent 10

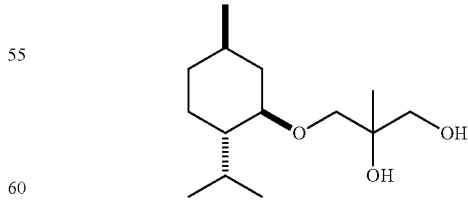

I-Menthoxy-2-methyl 1,2-propanediol 3-(I-Menthoxy)-1,2,propandiol is produced, for example, according to the following scheme on the basis of menthol (cf. U.S. Pat. No. 4,459,425, Takagaso):

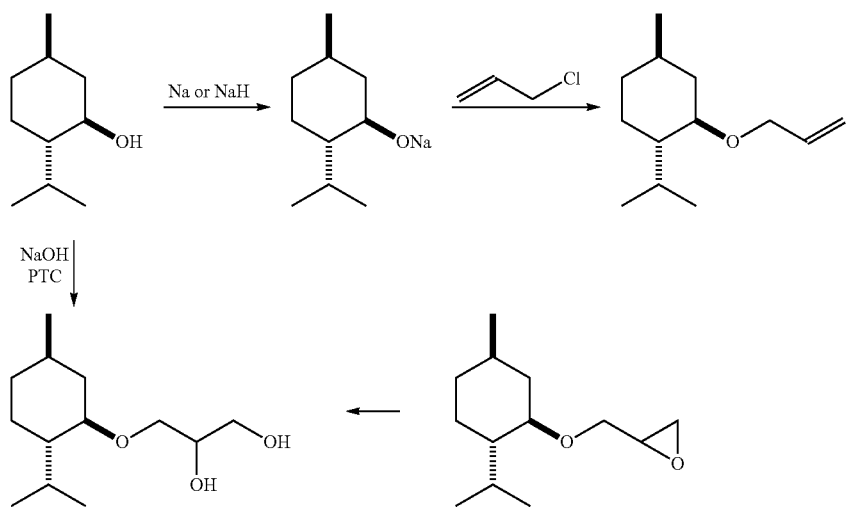

Alternative routes, in which menthol is reacted with epichlorohydrin in the first step, are described in U.S. Pat. Nos. 6,407,293 and 6,515,188 (Takagaso). An overview of preferred menthol compounds which are characterized by a CO bond is provided in the following:

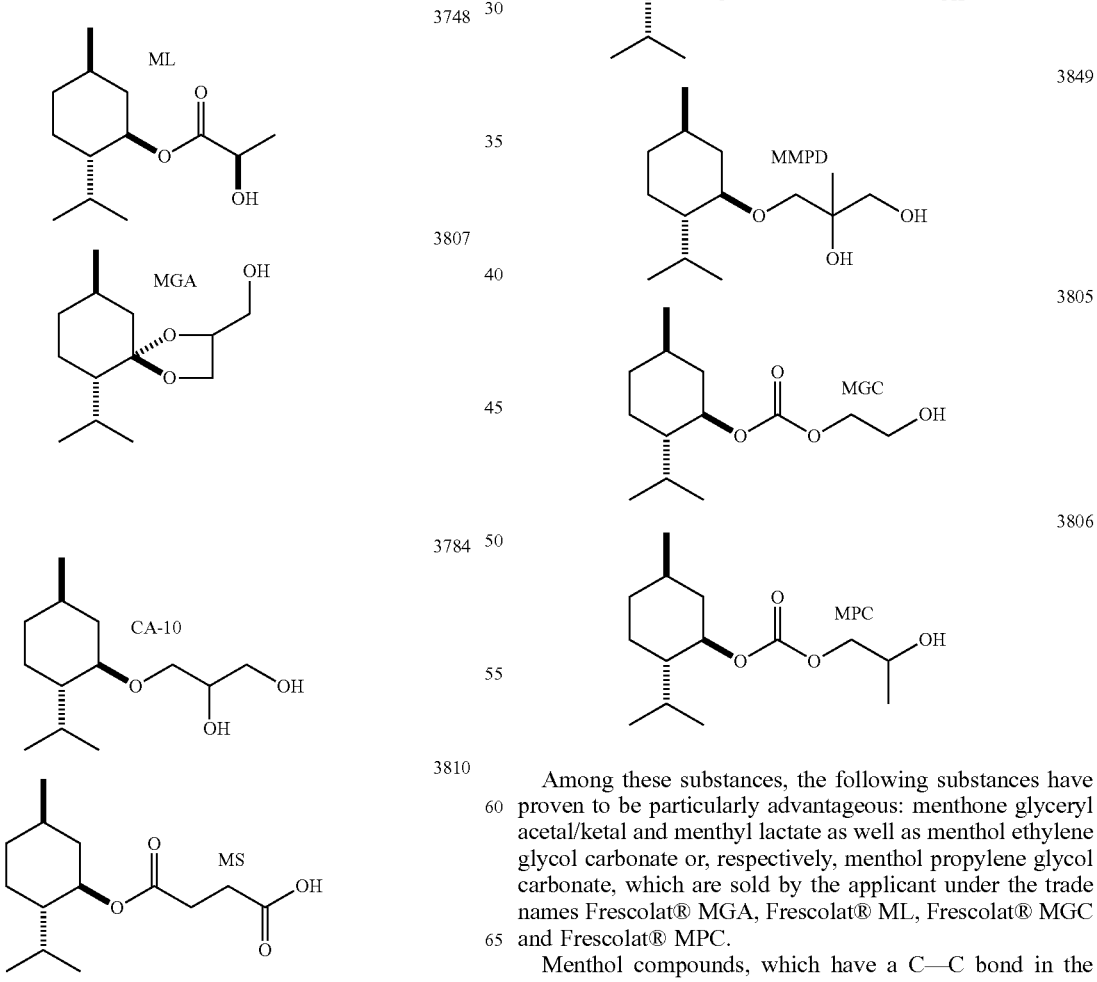

Among these substances, the following substances have proven to be particularly advantageous: menthone glyceryl acetal/ketal and menthyl lactate as well as menthol ethylene glycol carbonate or, respectively, menthol propylene glycol carbonate, which are sold by the applicant under the trade names Frescolat® MGA, Frescolat® ML, Frescolat® MGC and Frescolat® MPC.

Menthol compounds, which have a C—C bond in the 3-position were developed for the first time in the 1970ies.

Out of these, also a number of representatives within the meaning of the invention may be used. These substances are generally referred to as WS types. A menthol derivative forms the base body, in which the hydroxyl group is replaced by a carboxyl group (WS-1). All other WS types are derived from this structure such as, for example, the preferred species within the meaning of the invention WS-3, WS-4, WS-5, WS-12, WS-14 and WS-30. The two following illustrations show the synthesis paths:

diol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, dipropylene glycol, preferably 1,2-butylene glycol, 1,2-pentanediol and/or dipropylene glycol, and/or (ii-1) esters having 6 to 36 carbon atoms, preferably monoesters, diesters or triesters, preferably selected from the group consisting of diethyl phthalate, diethylhexyl 2,6-naphthalate, isopropyl myristate, isopropyl palmitate, iso-

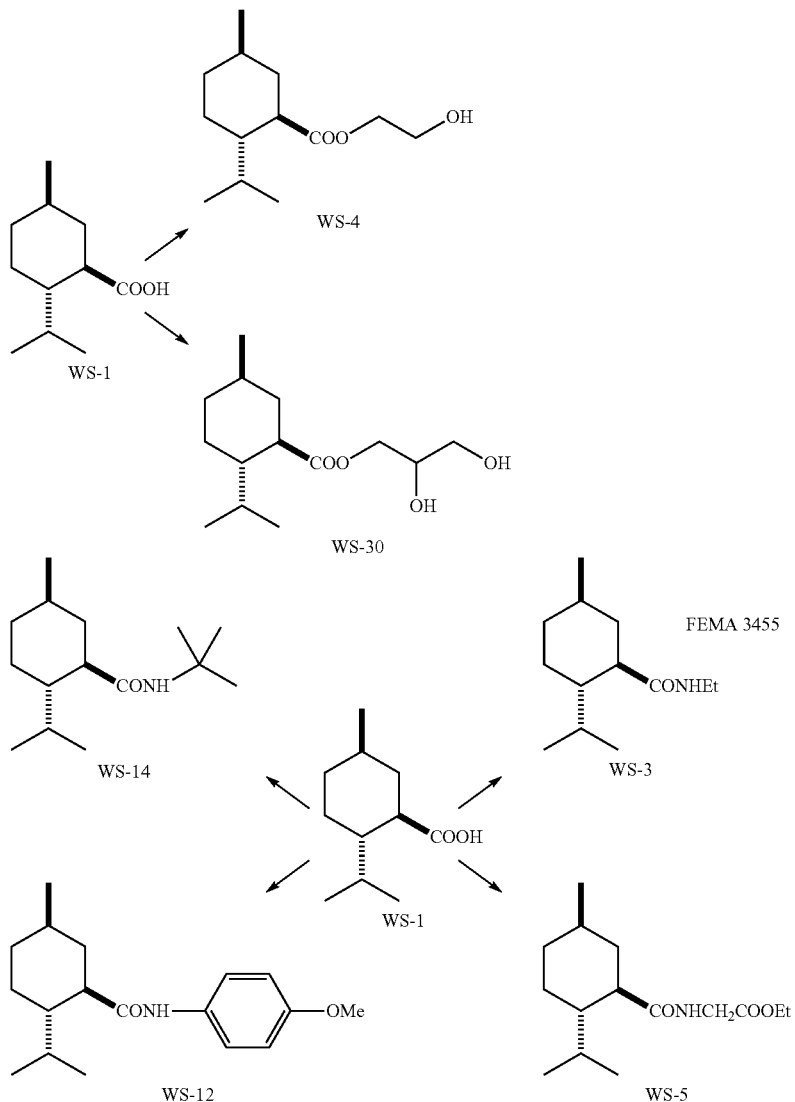

The esters derived from WS-1 are described, for example, in U.S. Pat. No. 4,157,384, and the corresponding N-substituted amides in J. Soc. Cosmet. Chem. S. 185-200 (1978).

Cosmetically Acceptable Carriers

The one or more cosmetically acceptable carriers of the present invention forming component (b) are preferably not water or ethanol, and more preferably are selected from the group comprising (alkane) diols having 3 to 10 carbon atoms, preferably selected from the group consisting of 1,2-propylene glycol, 2-methylpropane-1,3-diol, 1,2-butylene glycol, 1,3-butanepropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cetearyl ethylhexanoate, stearyl heptanoate, stearyl caprylate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, C12-i5-alkyl benzoates, cetyl palmitate, triethyl citrate, triacetin (triacetyl citrate), benzyl benzoate, benzyl acetate, vegetable oils (preferably olive oil, sunflower oil, soya oil, groundnut oil, rapeseed oil, almond oil, palm oil, coconut oil, palm kernel oil) and triglycerides, in particular glyceryl stearate, glyceryl triisononanoate, glyceryl laurate or triglycerides with identical or different C6 to C10 fatty acid radicals (so-called medium-chain triglycerides, in particular caprylic/capric triglyceride, like glyceryl tricaprylate, glyceryl tricaprate), and/or (ii-2) branched and unbranched alkyl or alkenyl alkohols, preferably selected from the group consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol) and cetearyl alcohol and behenyl alcohol, and/or (ii-3) branched and unbranched hydrocarbons and waxes, cyclic or linear silicone oils and dialkyl ethers having 6 to 24 carbon atoms, preferably selected from the group consisting of jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane and poly(methyl-phenyl siloxane.

Glycerine or isopropanol can also be used as carriers.

It has been surprisingly found, when the soothing composition according to the present invention is used before, during or after the application of cosmetic formulations with an alkaline pH-value, the caused skin irritation sensation, such as stinging, burning, tingling, tickling and skin tightness, can be intensively relieved/prevented. The mentioned alkaline cosmetic formulations can include, but are not limited to, hair colouring formulation, hair relaxing formulation, perm, depilatory, soap, shaving foam, toothpaste or dental fixative cream, sun protection, AP/Deodorants. Especially, during the application of hair colouration formulation and/or hair relaxing formulation, which can induce scalp irritation, especially sensitive scalp irritation, those uncomfortable symptoms can be significantly reduced through the use of the soothing composition of the present invention. It has also been observed that by using the soothing composition of the present invention the sensory profile of the hair treatment products, which are especially e.g. hair colouring products, can be improved without disadvantageous effect on the efficacy and/or quality of the hair treatment products.

Another object of the present invention is a cosmetic formulation (c) comprising a soothing composition of the present invention, wherein the cosmetic formulation (c) further comprises
(c-1) at least one separately provided oxidizing agent and
(c-2) at least one oxidation base, and optionally
(c-3) at least one coupler and/or
(c-4) at least one synthetic dye and/or
(c-5) at least one natural dye and/or
(c-6) an alkali
(c-7) adjuvants In one preferred embodiment of the present invention the above-mentioned cosmetic formulation (c) is a permanent hair dyeing formulation.

Permanent Hair Dyeing

In the present invention the term "permanent hair dyeing" refers to the application of a permanent dyeing formulation onto hair, which results in a permanent change of the hair colour. The process of permanent hair dyeing requires mixing two separately provided formulations (a colouring cream with an alkaline pH and a revealing cream with a pH<7) together just before the application onto the hair. The two are mixed immediately before use to give a pH of 9.5 required for the colouration process. The colouring cream contains the dye precursors (oxidation base and a coupler) and an alkali (usually ammonia or monoethanolamine) which opens up hair cuticles and acts as a vehicle for the dye precursors to move deep into the hair follicles. The revealing cream is the oxidizing agent (almost exclusively a stabilised hydrogen peroxide solution) to oxidise the dye precursors and to lighten the natural hair colour.

During the formulation is kept on the hair (usually 20 to 40 minutes) a series of chemical reactions between the colouring cream and the revealing cream take place, in which the most decisive reaction is the oxidization of the dye precursors (especially the oxidation base) by the oxidizing agent into larger dye molecules which would be trapped in the hair, whereby a permanent colouring effect is achieved.

Oxidizing Agents

The at least one oxidizing agent of the present invention is preferably chosen from hydrogen peroxide; urea peroxide; alkali metal ferricyanides or bromides; peroxygenated salts such as persulfates, perborates and percarbonates of alkali metals or alkaline earth metals, such as sodium, potassium and magnesium; or mixtures thereof. At least one redox enzyme(s) such as lactases, peroxidases and 2-electron oxidoreductases (such as uricase), optionally in the presence of the respective donor or cofactor thereof, may also be used as the at least one oxidizing agent.

The revealing cream containing the oxidizing agent may further comprise at least one basifying agent and/or at least one acidifying agent. For example, in one embodiment the at least one oxidizing agent comprises at least one acidifying agent. Examples of the at least one acidifying agent include, for example, organic or inorganic acids, such as hydrochloric acid, orthophosphoric acid, sulfuric acid, carboxylic acids such as acetic acid, tartaric acid, citric acid and lactic acid, and sulfonic acids.

The pH of the revealing cream containing is in one preferred embodiment, less than 7, for instance, if the oxidizing agent is hydrogen peroxide. The revealing cream may take the form of a solution, an emulsion or a gel.

Oxidation Base

The at least one oxidation dye precursor of the present invention is usually a oxidation base, which is preferably chosen from para-phenylenediamines, for instance, as described in patent applications FR-A-2766177 and FR-A-2766178, bis(phenyl)alkylenediamines, para-aminophenols as described, for example, in patent applications FR-A-2766177 and FR-A-2766178, ortho-aminophenols or cationic double bases such as derivatives of the bis(aminophenyl)alkylenediamine type described in patent application FR-A-2766179, ortho-phenylenediamines as described, for example, in patent applications FR-A-2782718, FR-A-2782716 and FR-A-2782719, and heterocyclic bases, and the corresponding salts thereof. These oxidation bases in combination with oxidizing products provide access to coloured species by a process of oxidative condensation.

Among the para-phenylenediamines non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis((β-hydroxyethyl)amino-2-methylaniline, 4-N,N-bis(β-hydroxyethyl)amino-2-chloroaniline, 2-p-hydroxyethyl-para-phenylenediamine, 2-fluoro-para-phenylenediamine, 2-isopropyl-para-phenylenediamine, N-((β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-((β,γ-dihydroxypropyl)-para-phenylenediamine, N-(4'-aminophenyl)-para-phenylenediamine, N-phenyl-para-phenylenediamine, 2-(β-hydroxyethyloxy-para-phenylenediamine, 2-O-acetyl-aminoethyloxy-para-phenylenediamine, N-((β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, 2-β-acetylaminoethyloxy-para-phenylenediamine and the corresponding salts thereof with an acid.

Among the bis(phenyl)alkylenediamines non-limiting mention may be made of, for example, N,N'-bis(β-hydroxyethyl)-N,N'-bis(4'-aminophenyl)-1,3-diaminopropanol, N,N'-bis((β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)-tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding salts thereof.

Among the para-aminophenols non-limiting mention may be made of, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the corresponding salts thereof with an acid.

Among the ortho-aminophenols non-limiting mention may be made of, for example, 2-aminophenol, 2-amino-5-methylphenol, 2-amino-6-methylphenol, and 5-acetamido-2-aminophenol, and the corresponding salts thereof.

Among the heterocyclic bases non-limiting mention may be made of, for example, 4,5-diamino-1-((B-hydroxyethyl) pyrazole and/or 2,3-diamino-6,7-dihydro-1H,5H-pyrazolo[1,2-a]pyrazol-1-one and the corresponding salts thereof, pyridine derivatives, pyrimidine derivatives, and pyrazole derivatives.

Among the pyridine derivatives non-limiting mention may be made of, for example, the compounds described, for example, in patents GB 1026978 and GB 1153196, for instance 2,5-diaminopyridine, 2-(4-methoxyphenyl)amino-3-amino-pyridine, and 3,4-diaminopyridine, and the corresponding salts thereof.

Other pyridine oxidation bases that may be useful in the compositions of the present invention are, for example, the 3-aminopyrazolo[1,5-a]pyridine oxidation bases or corresponding salts thereof described, for example, in patent application FR2801308. Examples that may be mentioned include pyrazolo[1,5-a]pyrid-3-ylamine, 2-acetylaminopyrazolo[1,5-a]pyrid-3-ylamine, 2-morpholin-4-yl pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl) methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a] pyridine-3,5-diamine, 5-morpholin-4-ylpyrazolo[1,5-a]pyrid-3-ylamine, 2-[(3-aminopyrazolo [1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a] pyridin-4-ol, 3-aminopyrazolo[1,5-a]pyridin-6-ol and 3-aminopyrazolo[1,5-a]pyridin-7-ol, and the corresponding salts thereof.

Among the pyrimidine derivatives, non-limiting mention may be made of, for example, the compounds described, for example, in patents DE 2359399; JP 88-169571; JP 05-63124; EP 0770375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the corresponding salts thereof, and the tautomeric forms thereof, when a tautomeric equilibrium exists.

Among the pyrazole derivatives non-limiting mention may be made of the compounds described, for example, in patents DE 3843892 and DE 4133957, and patent applications WO 94/08969, WO 94/08970, FR-A-2733749 and DE 19543988, for instance, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methyl-pyrazole, 4,5-diamino-1-(β-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4(β-hydroxyethyl) amino-1-methylpyrazole, and the corresponding salts thereof. 4,5-diamino-1-(β-methoxyethyl) pyrazole may also be used.

Other pyrazole derivatives that may be useful in the compositions of the present invention are, for example, diamino-N,N-dihydropyrazol-opyrazolones and those described in patent application FR 2886136, such as the following compounds and the corresponding salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2a] pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl) amino-6,7-dihydro-1H,5H-pyrazolo[1,2-a] pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-

(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo [1,2-a]pyrazol-1-one.

In one embodiment of the present invention, cationic oxidation bases of para-phenylene diamine structure are used, at least one of the amine functions of which is a tertiary amine bearing a pyrrolidine nucleus, the molecule comprising at least one quaternized nitrogen atom. Such bases are described, for example, in document EP-A-1348695.

Suitable primary intermediates include for example, p-phenylenediamine derivatives such as: benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl) benzene-1,4-diamine, 2-[(4-amino-phenyl-(2-hydroxyethyl)amino]-ethanol, (commonly known as N,N-bis(2-hydroxyethyl)-p-phenylenediamine) (2,5-diamino-phenyl)-methanol, 1-(2,5-diamino-phenyl)-ethanol, 2-(2,5-diaminophenyl)-ethanol, N-(4-amino-phenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, N4,N4,2-trimethylbenzene-1,4-diamine, 2-methoxy-benzene-1,4-diamine, 1-(2,5-diaminophe)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl) (2-hydroxyethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino] butyl}benzene-1,4-diamine, and 2-[2-(2-{2-[(2,5-diaminophenyl)-oxy] ethoxy}ethoxy)ethoxy]benzene-1,4-diamine; p-aminophenol derivatives such as: 4-aminophenol (commonly known as p-aminophenol), 4-methylamino-phenol, 4-amino-3-methyl-phenol, 4-amino-3-hydroxymethyl-phenol, 4-amino-2-methyl-phenol, 4-amino-2-[(2-hydroxyethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxyethyl)-phenol, 4-amino-3-(hydroxymethyl)phenol, 4-amino-3-fluoro-phenol, 4-amino-2-(aminomethyl)-phenol, and 4-amino-2-fluorophenol;

o-aminophenol derivatives such as: 2-aminophenol (commonly known as o-aminophenol), 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, N2,N2-dimethylpyridine-2,5-diamine, 2-[(3-amino-6-methoxypyridin-2-yl) amino]ethanol, 6-methoxy-N2-methyl-pyridine-2,3-diamine, 2,5,6-triaminopyrimidin-4(1H)-one, pyridine-2,5-diamine, 1-(4-methylbenzyl)-1H-pyrazole-4,5-diamine, 1-(benzyl)-1H-pyrazole-4,5-diamine, and 1-(4-chlorobenzyl)-1H-pyrazole-4,5-diamine.

Couplers

The optional at least one coupler of the present invention is preferably chosen from those conventionally used for the dyeing of keratin fibres.

Among the at least one coupler, non-limiting mention may be made of, for example, meta-phenylenediamines, meta-aminophenols, meta-diphenols, naphthalenic couplers and heterocyclic couplers, and also the corresponding salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxy-pyridine, 1-N-β-hydroxyethylamino-3,4-methylenedioxy-benzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a] benzimidazole, the corresponding salts thereof with an acid, and mixtures thereof.

In general, the corresponding salts of the at least one oxidation base and at least one coupler that may be used in the context of the present invention may be chosen from the corresponding salts with an acid such as the hydrochlorides, hydrobromides, sulfates, citrates, succinates, tartrates, lactates, tosylates, benzenesulfonates, phosphates and acetates.

Synthetic Dyes

Non-limiting examples of the optional at least one synthetic direct dye of the present invention include, for example, the following direct dyes: azo direct dyes; methine direct dyes; carbonyl dyes; azine direct dyes; nitrobenzenic direct dyes; phthalocyanine and porphyrin direct dyes; quinone direct dyes, and in particular anthraquinone, azomethine direct dyes, tri(hetero)arylmethane direct dyes; indoamine direct dyes; indigoid direct dyes; nitro(hetero)aryl dyes; xanthene direct dyes; naphthoquinone or benzoquinone dyes; diazacarbocyanines and isomers thereof and tetraazacarbocyanines (tetraazapentamethines); alone or as mixtures.

For example, the azo dyes may comprise an —N═N— function where the two nitrogen atoms are not simultaneously engaged in a ring. However, it is not excluded for one of the two nitrogen atoms of the sequence —N═N— to be engaged in a ring. The azo direct dyes comprise the following dyes, which are described in the Colour Index International, 3rd edition: Disperse Red 17; Disperse Red 13; Basic Red 22; Basic Red 76; Basic Yellow 57; Basic Brown 16; Basic Brown 17; Disperse Green 9; Disperse Black 9; Solvent Black 3; Disperse Blue 148; Disperse Violet 63; Solvent Orange 7; 1-(4'-aminodiphenylazo)-2-methyl-4-bis (p-hydroxyethyl)aminobenzene (INCI name: HC Yellow 7).

The dyes of the methine family comprise compounds comprising at least one sequence selected from >C═C< and —N═C< wherein the two atoms are not simultaneously engaged in a ring. However, it is pointed out that one of the nitrogen or carbon atoms of the sequences may be engaged in a ring. For example, the dyes of this family are derived from compounds of true methine type (comprising at least one above mentioned sequence —C═C—); of azomethine type (comprising at least one, or more, sequences —C═N—) with, for example, azacarbocyanines and their isomers, diazacarbocyanines and their isomers, and tetraazacarbocyanines; of mono- and diarylmethane type; of indoamine (or diphenylamine) type; of indophenol type; or of indoaniline type.

With regard to the dyes of the carbonyl family, non-limiting mention may be made of, for example dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigold, thioindigo, naphthalimide, anthrapyrimidine, diketopyrrolopyrrole and coumarin dyes.

With regard to the dyes of the azine family, non-limiting mention may be, for example, azine, xanthene, thioxanthene, fluorindine, acridine, (di)oxazine, (di)thiazine, pyronin dyes, Basic Blue 17, Basic Red 2, and Solvent Orange 15.

The nitrobenzenic direct dyes may be chosen from, for example, nitrobenzene and nitropyridine direct dyes, mention may be made in a non-limiting manner of the following compounds: 1,4-diamino-2-nitrobenzene; 1-amino-2-nitro-4-β-hydroxyethylaminobenzene; 1-amino-2-nitro-4-bis(β-hydroxyethyl)aminobenzene; 1,4-bis(β-hydroxyethyl-amino)-2-nitrobenzene; 1-β-hydroxyethylamino-2-nitro-4-bis(β-hydroxyethyl-amino)benzene; 1-β-hydroxyethylamino-2-nitro-4-aminobenzene; 1-β-hydroxyethylamino-2-nitro-4-(ethyl) (β-hydroxyethyl) aminobenzene; 1-amino-3-methyl-4-β-hydroxyethylamino-6-nitrobenzene; 1-amino-2-nitro-4-β-hydroxyethylamino-5-chlorobenzene; 1,2-diamino-4-nitrobenzene; 1-amino-2-β-hydroxyethylamino-5-nitrobenzene; 1,2-bis(β-hydroxyethylamino)-4-nitrobenzene; 1-amino-2-tris (hydroxymethyl)methylamino-5-nitro-benzene; 1-hydroxy-2-amino-5-nitrobenzene, 1-hydroxy-2-amino-4-nitrobenzene; 1-hydroxy-3-nitro-4-aminobenzene; 1-hydroxy-2-amino-4,6-dinitrobenzene; 1-β-hydroxy-ethyloxy-2-β-hydroxyethylamino-5-nitrobenzene, 1-methoxy-2-β-hydroxyethylamino-5-nitrobenzene; 1-β-hydroxyethyloxy-3-methylamino-4-nitrobenzene; 1-β,γ-dihyclroxypropyloxy-3-methylamino-4-nitrobenzene; 1-β-hydroxyethylamino-4-β,γ-dihydroxypropyloxy-2-nitrobenzene; 1-β,γ-dihydroxypropylamino-4-trifluoromethyl-2-nitrobenzene; 1-β-hydroxyethylamino-4-trifluoromethyl-2-nitrobenzene; 1β-hydroxyethylamino-3-methyl-2-nitrobenzene; 1-β-aminoethylamino-5-methoxy-2-nitrobenzene; 1-hydroxy-2-chloro-6-ethylamino-4-nitrobenzene; 1-hydroxy-2-chloro-6-amino-4-nitrobenzene; 1-hydroxy-6-bis(β-hydroxyethyl)amino-3-nitrobenzene; 1-β-hydroxy-ethylamino-2-nitrobenzene; 1-hydroxy-4-β-hydroxyethylamino-3-nitrobenzene.

With regard to the dyes of porphyrin or phthalocyanine type, it is possible to use cationic or non-cationic compounds, optionally comprising at least one metal or metal ions, for instance alkali metals, alkaline-earth metals, zinc and silicon.

Among the quinone direct dyes non-limiting mention may be made of, for example, the following dyes: Disperse Red 15; Solvent Violet 13; Solvent Blue 14; Disperse Violet 1; Disperse Violet 4; Disperse Blue 1; Disperse Violet 8; Disperse Blue 3; Disperse Red 11; Disperse Blue 7; Disperse Blue 14; Basic Blue 22; Disperse Violet 15; Disperse Blue 377; Disperse Blue 60; Basic Blue 99. It is also possible to mention the following compounds: 1-N-methylmorpholiniumpropylamino-4-hydroxyanthraquinone; 1-aminopropylamino-4-methylaminoanthraquinone; 1-aminopropylaminoanthraquinone; 5-β-hydroxyethyl-1,4-diaminoanthraquinone; 2-aminoethylaminoanthraquinone; 1,4-bis(β,γ-dihydroxypropylamino)anthraquinone, and also the coumarin compound Disperse Yellow 82.

Among the triarylmethane dyes that may be used according to the present invention, non-limiting mention may be made of, for example, the following compounds: Basic Green 1: Basic Violet 3; Basic Violet 14; Basic Blue 7; and Basic Blue 26.

Among the indoamine dyes that may be used according to the present invention, non-limiting mention may be made of, for example, the following compounds: 2-β-hydroxyethyl-amino-5-[bis(β-4'-hydroxyethyl)amino]anilino-1,4-benzoquinone; 2-β-hydroxyethylamino-5-(2'-methoxy-4'-amino) anilino-1,4-benzoquinone; 3-N(2'-chloro-4'-hydroxy) phenylacetylamino-6-methoxy-1,4-benzoquinone imine; 3-N(3'-chloro-4'-methylamino)phenylureido-6-methyl-1,4-benzoquinone imine; and 3-[4'-N-(ethylcarbamylmethyl) amino]phenylureido-6-methyl-1,4-benzoquinone imine.

These dyes may be monochromophoric dyes (i.e. comprising only one dye) or polychromophoric, for example di- or trichromophoric, dyes; the chromophores may be identical or different, and from the same chemical family or otherwise. It should be noted that a polychromophoric dye comprises two or more radicals each derived from a molecule that absorbs in the visible region between 400 and 800 nm. Furthermore, this absorbance of the dye does not require any prior oxidation thereof, or combination with any other chemical species.

In the case of polychromophoric dyes, the chromophores are connected together by means of at least one linker, which may be cationic or non-cationic.

Natural Dyes

The optional at least one natural dye can be chosen from lawsone, juglone, alizarin, purpurin, carminic acid, kermesic acid, purpurogallin, isatin, indigo, protocatechaldehyde, anthocyans, anthocyanidins, curcumin, orceins and apigenidin.

Adjuvants

Suitable adjuvants encompass anionic, cationic, non-ionic, amphoteric or zwitterionic polymers or mixtures thereof; mineral thickeners, for example fillers such as clays or talc; organic thickeners, for instance anionic, cationic, non-ionic and amphoteric polymeric associative thickeners; antioxidants, penetrants, Sequestrants, fragrances; dispersants; film-forming agents; ceramides, preservatives, opacifiers; conditioning agents, for example in combination with cationic polymers. The above adjuvants may general by present in an amount, for each of them, ranging from 0.01% to 20% wt.-% relative to the weight of the composition.

Compositions

In one preferred embodiment of the present invention the soothing composition is present in a cosmetic formulation (c) in an amount from 0.01 to 20 wt. %, preferably from 0.1 to 10 wt. %, more preferably 0.3 to 5 wt. %, and even more preferably from 0.5 to 3 wt. %.

In another preferred embodiment of the present invention the at least one oxidation base (c-2) is present in a cosmetic formulation (c) in an amount from 0.0001 to 10 wt. %, and the at least one separately provided oxidizing agent (c-1) is preferably present in an amount from 5 to 95 wt. %

In a further preferred embodiment of the present invention the cosmetic formulation (c) further comprises the at least one coupler (c-3) in an amount from 0.0001 to 10 wt. %; the at least one synthetic dye (c-4) in an amount from 0.005 to 20 wt. %; and the at least one natural dye (c-5) in an amount from 0.005 to 20 wt. %.; alkali (c-6) in an amount from 0.1 to 30 wt. %; adjuvants (c-7) in an amount from 0.01 to 20 wt. %

The cosmetic formulation (c) of the present invention, which is preferably a permanent hair dyeing formulation, possesses comfortable sensory profile as well as good colouring quality and intensity.

Another object of the present invention is a cosmetic formulation (d) comprising a soothing composition of the present invention, wherein the cosmetic formulation (d) comprises (d-1) at least one synthetic direct dye.

In one preferred embodiment of the present invention the above-mentioned cosmetic formulation (d) is a semi-permanent hair dyeing formulation.

Semi-Permanent Hair Dyeing

Another colouring method is the semi-permanent dyeing. This method comprises the application of a semi-permanent dyeing formulation, which usually comprises direct dyes, to the keratin fibers. In contrast to the above mentioned permanent hair dyeing, the dyes in such a formulation can only partially penetrate into the hair shaft, while the rest most dye molecule affinity dyes attach to the surface of the keratin fibers. For this reason, the obtained colour will survive repeated washing, typically 4-5 shampoos or a few weeks.

Synthetic Direct Dye

The synthetic direct dyes used in cosmetic formulation (d) of the present invention include all the substances listed under (c-4) Synthetic Direct dyes In one preferred embodiment of the present invention the soothing composition are present in the cosmetic formulation (d) in an amount from 0.01 to 20 wt. %, preferably from 0.1 to 10 wt. %, more preferably 0.3 to 5 wt. %, and even more preferably from 0.5 to 3 wt. %.; and (d-1) the at least one synthetic direct dye in an amount from 0.0005 to 20 wt. %.

Another object of the present invention is a cosmetic formulation (e) comprising a soothing composition of the present invention, wherein the cosmetic formulation (e) further comprises
(e-1) at least one alkaline agent, and optionally
(e-2) at least one oleaginous material and/or
(e-3) at least one additive.

In one preferred embodiment of the present invention the above-mentioned cosmetic formulation (e) is a hair relaxing formulation.

Hair Relaxing

In the present invention the term "hair relaxing and/or straightening" means lanthionizing keratin fibers. Relaxing or straightening of hair can be achieved by disrupting the disulfide bonds of the hair fibers with an alkaline agent or a reducing agent. The chemical disruption of disulfide bonds by an alkaline agent is usually combined with mechanical straightening of the hair, such as combing, and straightening generally occurs due to changes of the relative positions of opposite polypeptide chains within the hair fiber. The reaction is generally terminated by rinsing and/or the application of a neutralizing composition.

Alkaline Agents

The alkaline agent of the present invention usually functions as a hydroxide ion generator and is preferably chosen from those compositions that produce hydroxide ions appropriate for the lanthionization of hair. As used herein, "hydroxide ion generator" refers to both compounds and compositions that generate hydroxide ions, and compounds and compositions that comprise hydroxide ions. Hydroxide ion generators may, for example, be chosen from traditional "lye" and "no lye" hair relaxer compositions and other soluble or slightly soluble hydroxide ion sources. "Lye" relaxers contain sodium hydroxide; in "no lye" relaxers the source of active hydroxide is an alkaline agent other than sodium hydroxide, including, for example, other soluble metal hydroxides, for example, alkali metal hydroxides such as lithium and potassium hydroxide, as well as less soluble multivalent metal hydroxides, for example $Ca(OH)_2$, that are converted, in situ, to soluble active bases, e.g., guanidine hydroxide.

Non-limiting examples of less soluble or insoluble hydroxide ion generators include calcium hydroxide, barium hydroxide, magnesium hydroxide, aluminum hydroxide, cupric hydroxide, strontium hydroxide, molybdenum hydroxide, manganese hydroxide, zinc hydroxide, cobalt hydroxide, and the like. The complexing agents that may be used in the practice of this disclosure include, but are not limited to, mono-, di-, poly-amino-, and hydroxy-carboxylic acids, mono-, di-, poly-, amino- and hydroxy-sulfonic acids and mono-, di-, poly-, amino- and hydroxy-phosphonic acids. Other suitable complexing agents are chelating agents and sequestering agents. Non-limiting examples of complexing agents include ethylene-diaminetetraacetic acid (EDTA), N-(hydroxyethyl)ethylene diamine triacetic acid, aminotrimethylene phosphonic acid, diethylenetriaminepentaacetic acid, lauroyl ethylene diamine triacetic acid, nitriloacetic acid, iminodisuccinic acid, tartaric acid, citric acid, N-2-hydroxyethyliminodiacetic acid, and the like. The complexing agents may be used in the form of their corresponding organic and/or inorganic salts, with guanidine salts being exemplary of the corresponding organic salts, and potassium, sodium and/or lithium salts being exemplary of the inorganic salts. U.S. Pat. No. 65,612,327 is incorporated herein by reference with respect to its disclosure of the activation of multivalent metal hydroxides through the use of a complexing agent. Preferred hydroxide ion generators are strong water-soluble bases, particularly preferred is sodium hydroxide.

Oleaginous Material

The optional at least one oleaginous material of the present invention is such as mineral oil or petrolatum.

In one preferred embodiment of the present invention the soothing composition is present in a cosmetic formulation (e) in an amount from 0.01 to 20 wt. %, preferably from 0.1 to 10 wt. %, more preferably 0.3 to 5 wt. %, and even more preferably from 0.5 to 3 wt. %.; and (e-1) the at least one alkaline agent is preferably present in an amount from 0.5 to 20 wt. %;

In a further preferred embodiment of the present invention the cosmetic formulation (e) further comprises the at least one oleaginous material (e-2) in an amount from 0.0001 to 10 wt. %; and the at least one additive (e-3) in an amount from 0.0005 to 20 wt. %.

Another object of the present invention is a cosmetic formulation (f) comprising a soothing composition of the present invention, wherein the cosmetic formulation (f) further comprises
(f-1) at least one monoglyceride having C16 to C22 alkyl ester group, and optionally
(f-2) at least one conditioning surfactant.

In one preferred embodiment of the present invention the above-mentioned cosmetic formulation (f) is a hair post-treatment formulation.

Hair Post-Treatment

The term post-treatment refers to a treatment applied to the hair after the above-mentioned lanthionization process, i.e. applying a post-treatment composition to the lanthionized hair, to make the rough and unconditioned hair after relaxing and/or straightening be felt smooth and soft.

Monoglycerides

The monoglyceride having $C_{16}$ to $C_{22}$-alkyl ester group of the present invention preferably has a long chain unsaturated group. More preferably the used monoglyceride is glyceryl monololeate.

Conditioning Surfactants

The optional at least one conditioning surfactant of the present invention are cosmetically acceptable and suitable for topical application to the hair. Preferably the conditioning surfactants are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants include: quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride Quaternium-5, Quaternium-31, Quaternium-18 and mixtures thereof.

The most preferred cationic surfactants for conditioner compositions of the present invention are monoalkyl quaternary ammonium compounds in which the alkyl chain length is C8 to C14.

Typical monoalkyl quaternary ammonium compounds for use in the post-treatment compositions of the invention include (i) lauryl trimethylammonium chloride; (ii) cocodimethyl benzyl ammonium chloride; (iii) PEG-n lauryl ammonium chlorides (where n is the PEG chain length), such as PEG-2 cocomonium chloride, PEG-2 cocobenzyl ammonium chloride, PEG-5 cocomonium methosulphate, PEG-15 cocomonium chloride, compounds like lauryldimethylhydroxyethylammonium chloride, and mixtures of any of the foregoing cationic surfactants compounds.

In one preferred embodiment of the present invention the soothing composition is present in the cosmetic formulation (f) in an amount from 0.01 to 20 wt. %, preferably from 0.1 to 10 wt. %, more preferably 0.3 to 5 wt. %, and even more preferably from 0.5 to 3 wt. %.; and (f-1) the at least one monoglyceride is preferably present in an amount from 1 to 10 wt %, more preferably from 3.5 to 7.5 wt %.

In a further preferred embodiment of the present invention the cosmetic formulation (f) further comprises the at least one conditioning surfactant (f-2) is preferably from 0.01 to 10 wt. %, more preferably from 0.1 to 5 wt. %, and the weight ratio of the conditioning surfactant (f-2) to monoglyceride (f-1) is preferably from 1:10 to 10:1, more preferably from 1:5 to 5:1, optimally from 1:1 to 1:7, for example 1:3.

In a preferred embodiment the above-mentioned cosmetic formulation (f) comprises (f-2) at least one conditioning surfactant, and/or
(f-3) at least one fatty alcohol material and/or
(f-4) at least one cationic polymer and/or
(f-5) at least one oily conditioning agent and/or
(f-6) at least one adjuvant Fatty Alcohol Material By "fatty alcohol material" is meant a fatty alcohol, an alkoxylated fatty alcohol, or a mixture thereof. Representative fatty alcohols comprise from 8 to 22 carbon atoms, more preferably 16 to 20. Examples of suitable fatty alcohols include cetyl alcohol, stearyl alcohol and mixtures thereof. Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

In one preferred embodiment of the present invention the fatty alcohol material (f3) is present in the cosmetic formulation (f) in an amount from 0.1 to 10, and more preferably from 0.1 to 5 wt %. The weight ratio of the conditioning surfactant (f-2) to the fatty alcohol material (f-3) is preferably from 10:1 to 1:10, more preferably from 4:1 to 1:8, and optimally from 1:1 to 1:7, for example 1:3.

Cationic Polymers

The optional cationic polymer of the present invention may be emulsified droplets of a silicone conditioning agent, for enhancing conditioning performance. The silicone is insoluble in the aqueous matrix of the composition and so is present in an emulsified form, with the silicone present as dispersed droplets. Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst. In general it has been found that conditioning performance increases with increased viscosity. Accordingly, the viscosity of the silicone itself is preferably at least 600,000 cst, most preferably at least 500,000 cst, ideally at least 1,000,000 cst. Preferably the viscosity does not exceed 10<9> cst for ease of formulation.

Emulsified silicones for use in the post-treatment compositions of the invention will typically have an average silicone droplet size in the composition of less than 30, preferably less than 20, more preferably less than 10 µm. It has been found that reducing the droplet size generally improves conditioning performance. Most preferably the average silicone droplet size of the emulsified silicone in the composition is less than 2 µm, ideally it ranges from 0.01 to 1 µm. Silicone emulsions having an average silicone droplet size of <=0.15 µm are generally termed microemulsions.

Suitable silicone emulsions for use in the invention are also commercially available in a pre-emulsified form. Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in the post-treatment compositions of the present invention are amino functional silicones. By "amino functional silicone" is meant a silicone containing at least one primary, secondary or tertiary amine group, or a quaternary ammonium group. Examples of suitable amino functional silicones include (i) polysiloxanes having the CTFA designation "amodimethicone", polysiloxanes termed "trimethylsilylamodimethicone" (iii) quaternary silicone polymers as described in EP-A-0 530 974.

Amino functional silicones suitable for use in the post-treatment compositions of the present invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since it has been found that too high amine concentration can be detrimental to total silicone deposition and therefore conditioning performance. The viscosity of the amino functional silicone is not particularly critical and can suitably range from about 100 to about 500,000 cst. Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non-ionic and/or cationic surfactant.

Oily Conditioning Agents

The optional oily conditioning agent of the present invention is a dispersed, non-volatile, water-insoluble oily agent, which will be dispersed in the composition in the form of droplets and form a separate, discontinuous phase from the aqueous, continuous phase of the composition. In other words, the oily conditioning agent will be present in the cosmetic composition in the form of an oil-in-water emulsion. By "water-insoluble" is meant that the material is not soluble in water (distilled or equivalent) at a concentration of 0.1% (w/w), at 250° C. Suitably, the D32 average droplet size of the oily conditioning component is at least 0.4, preferably at least 0.8, and more preferably at least 1 µm. Additionally, the D32 average droplet size of the oily conditioning component is preferably no greater than 10, more preferably no greater 8, more preferably no greater than 5, yet more preferably no greater than 4, and most preferably no greater than 3.5 µm. The oily conditioning agent may suitably be selected from oily or fatty materials, and mixtures thereof.

Preferred oily and fatty materials will generally have a viscosity of less than 5 Pa·s, more preferably less than 1 Pa·s, and most preferably less than 0.5 Pa·s, e.g. 0.1 Pa·s and under as measured at 25° C. With a Brookfield Viscometer (e.g. Brookfield RV) using spindle 3 operating at 100 rpm.

Oily and fatty materials with higher viscosities may be used. For example, materials with viscosities as high as 65 Pa·s may be used. The viscosity of such materials (i.e. materials with viscosities of 5 Pa·s and greater) can be measured by means of a glass capillary viscometer as set out further in Dow Corning Corporate Test Method CTM004, Jul. 20, 1970. Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as C2-C6 alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250" G. to 300" G. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters thereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20. Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms. The monocarboxylic acid ester need not necessarily contain at least one chain with at least 10 carbon atoms, so long as the total number of aliphatic chain carbon atoms is at least Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of C4-C8 dicarboxylic acids such as C1-C22 esters (preferably C1-C6) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di- and triglycerides.

Particularly preferred fatty esters are mono-, di- and triglycerides, more specifically the mono-, di-, and tri-esters of glycerol and long chain carboxylic acids such as C1-C22 carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate. Specific examples of preferred materials include cocoa butter, palm stearin, sunflower oil, soybean oil and coconut oil.

In one preferred embodiment of the present invention the oily conditioning agent (f-5) present in the cosmetic formulation (f) is preferably present in an amount from 0.05 to 10 wt. %, more preferably from 0.2 to 5 wt. %, more preferably from about 0.5 to 3 wt. %.

The above mentioned cosmetic formulation of the present invention (f) may be provided as a multicomponent kit comprising at least two separate components. A first component of the kit contains comprises at least one composition for generating hydroxide ions to relax the hair. The second component comprises at least one composition comprising at least one basic amino acid.

When the above mentioned cosmetic formulations comprising a soothing composition of the present invention, which are preferably permanent hair dyeing formulation, semi-permanent hair dyeing formulation, hair relaxing and/or straightening formulation and hair post-treatment formulation respectively, are used, intensively improved scalp sensation is observed and the storage stability as well as the dispersion property of these formulations of the present invention would be improved, while their intrinsic characters were not be depressed.

Method

Another object of the present invention is a method of permanent hair dyeing, comprising the following steps
(i-1) mixing a soothing composition of the present invention with a permanent hair dyeing product, and applying the obtained mixture onto the hair; or
(i-2) applying a cosmetic formulation (c) of the present invention onto the hair;
(ii) leaving the mixture of step (i-1) or (i-2) on the hair for a define time; then
(iii) rinsing the hair.

Another object of the present invention is a method of semi-permanent hair dyeing, comprising the following steps
(i-1) mixing a soothing composition of the present invention with a semi-permanent hair dyeing product, and applying the obtained mixture onto the hair; or
(i-2) applying a cosmetic formulation (d) of the present invention onto the hair;
(ii) leaving the mixture of step (i-1) or (i-2) on the hair for a define time; then
(iii) rinsing the hair.

The preferable permanent hair dyeing product and semi-permanent hair dyeing product, which could be used in the present invention, are all commercial available products for permanent and semi-permanent hair colouring, such as for example:

Permanent

L'Oréal Excellence Crème
L'Oréal Ganier Nutrisse
L'Oréal Préférence
L'Oréal Prodigy
Schwarzkopf Perfect Mousse
Schwarzkopf Nectra Colour
Schwarzkopf Palette
Schwarzkopf Igora
Revlon ColourSilk
Softsheen Carson Dark & Lovely Semi-Permanent (Non-Oxidative, No Ammonia)

L'Oréal Dédicace
L'Oréal Ganier Herbashine
Procter & Gamble Clairol Natural Instincts Another object of the present invention is a method of hair relaxing comprising the following steps
(i-1) mixing a soothing composition of the present invention with a hair relaxing product, and applying the obtained mixture onto the hair; or (i-2) applying a cosmetic formulation (e) of the present invention onto the hair;

(ii) leaving the mixture of step (i-1) or (i-2) on the hair for a define time; then (iii) rinsing the hair.

The preferable hair relaxing product, which could be used in the present invention, are described in publications including U.S. Pat. Nos. 4,324,263, 4,390,033, 5,476,650, 5,849,277, US 2003/0175233, a for example:

Softsheen Carson Dark & Lovely No-Lye Relaxer

African Pride Olive Miracle Conditioning Anti-Breakage Hair Relaxer

Dr. Miracle's "Feel It" Formula Thermalceutical Intensive No-Lye Hair Relaxer Kit Softsheen Carson Optimum Care Salon Collection Optimum Care Anti-Breakage No-Lye Relaxer System, Regular Another object of the present invention is a method of hair post-treatment, comprising the following steps (i-1) mixing a soothing composition of the present invention with a hair post-treatment product, and applying the obtained mixture onto the hair; or (i-2) applying a cosmetic formulation (f) of the present invention onto the hair;

(ii) leaving the mixture of step (i-1) or (i-2) on the hair for a define time; then (iii) rinsing the hair.

The preferable hair post-treatment product, which could be used in the present invention, are all commercial available products for hair post-treatment, such as Those sold in the kit of the following relaxing kits:

Softsheen Carson Dark & Lovely No-Lye Relaxer

African Pride Olive Miracle Conditioning Anti-Breakage Hair Relaxer

Dr. Miracle's "Feel It" Formula Thermalceutical Intensive No-Lye Hair Relaxer Kit Softsheen Carson Optimum Care Salon Collection Optimum Care Anti-Breakage No-Lye Relaxer System, Regular Another object of the present invention is the use of a soothing composition of the present invention for the manufacture of cosmetic formulations with an alkaline pH between 6.5 to 12.

The cosmetic formulations with an alkaline pH between 6.5 to 12 is selected for example from hair colouring formulation, hair relaxing and/or straightening formulation, hair post-treatment formulation, toothpastes, shaving foams, sun care, deodorants or any emulsion with a pH between 6.5 to 12.

Another object of the present invention is the use of a soothing composition of the present invention for depressing uncomfortable sensation on skin and/or on scalp during the application of alkaline cosmetic formulations, wherein the cosmetic formulations are preferably hair colouring formulations, hair relaxing and/or straightening formulations, perms, depilatories and soaps, toothpastes, shaving foams, sun care, deodorants or any emulsion with a pH between 6.5 to 12.

The uncomfortable sensation on skin and/or on scalp generally includes stinging, burning, tingling, tickling and skin tightness.

Finally, another object of the present invention is the use of menthol compounds according to formula (II) and/or (III)

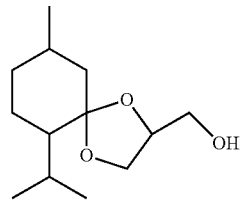

(II)

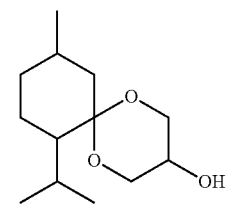

(III)

as soothing agent.

EXAMPLES

Evaluation Study

Samples and Subjects

The soothing compositions applied in the study comprise 100 wt. % Frescolat MGA and 0 wt. % carrier ingredient and evaluated in a simple blind and intra-individual study, which was done on 2 parallel groups of 24 subjects; each subject was her own control. The criteria of the subjects are listed in Table 1.

TABLE 1

Specific criteria for the subjects

Sex: female.
Age: between 25 and 40.
Phototype: at least IV according to Fitzpatrick.
Subject having a sensitive scalp.
Subject being accustomed to colour her hair (at home or hairdressing salon).
Subject agreeing to have her hair coloured by the hairdresser at the laboratory.

Procedure of the Evaluation Study

The evaluation study was carried out by a hairdresser at a laboratory in successive steps comprising:

Preparing the hair colouring mixture by mixing all the content of L'Oréal Excellence Crème 4.15 Marron Frappé Colouring cream enriched with pro-kératine (FILC33956/1) (tube 48 ml) in the Revealing cream (FILC13169/25) (plastic bottle 72 ml) a colouring tube with a developer bottle Applying on dry hair. Applying the L'Oréal Excellence Crème 4.15 Marron Frappé Protective serum Pre-colouration with Céramide (Plastic tube 12 ml) (FIL51515/1) on damaged parts of the hair especially on the ends. Do not wash out. (iv) Parting the hair with the nozzle of the tube and applying the mixture of (i) in sections, gently massaging and letting it rest for 30 minutes;

(v) Rinsing the hair;
(vi) Applying the L'Oréal Excellence Crème 4.15 Marron Frappé Conditioner Post-colouration (plastic bottle 44 ml) (FIL C52825/1)

Evaluation Criteria

Evaluation of the protective effect of the soothing compositions comprising Frescolat MGA was tested by the assessment with 5-point scales of cutaneous signs, including tightness, stinging, itching/pruritus, warm/burning sensation, discomfort and so on, felt by the subjects during hair colouring, in comparison with the placebo (hair colouring single).

This evaluation occurred at 3 kinetics times: during the application (T1, maximum intensity will be retained); at the end of the hair colouring application (T2, before the waiting time); and after the 30-minute-waiting time (T3, before rinsing). The confrontation of these results, in comparison with the placebo, was used to conclude the protective effect of the studied ingredient (see Table 3 and Table 4).

After hair colouring, the hairdresser evaluated the influence of the ingredient on the shade obtained, including shade intensity and respect of the attempted shade. For each parameter assessed by the hairdresser, the same method described above was used (see Table 5).

A questionnaire was filled by the subjects after application of the product to subjectively evaluate the efficacy of the ingredient (see Table 6).

Data Analysis

For each parameter, the descriptive statistics for quantitative data (number of valid values, number of missing values, mean, median, and standard deviation, standard error of the mean, minimum and maximum values) were computed and tabulated by product and by time point.

For each time point, a one way ANOVA (with factor product as fixed) was fitted to raw data. The contrasts of interest were built to compare each combination with the colouring hair applied alone.

The underlying assumptions of the model were checked (Gaussian distribution and homoscedasticity of residuals). In case of strong deviation, a non-parametric approach was used.

For all analyses, the type I error was set at $\alpha=0.05$ in a two tailed approach when applicable.

Evaluation Results

The comparisons between the sample comprising the soothing composition of the present invention and Placo (control) are listed in the following tables.

Table 2 shows the results of the number and percentage of subjects presenting an uncomfortable reaction at three evaluating times (T1-3).

TABLE 2

| | | Application results | | | |
|---|---|---|---|---|---|
| | | Amount of Subjects with reactions | | | Subjects with reactions to uncomfortable |
| | cutaneous signs | T1 | T2 | T3 | sensation % |
| Sample | Tightness | 0 | 0 | 0 | 0 |
| | Stinging | 2 | 3 | 2 | 21 |
| | Itching/Pruritus | 0 | 0 | 0 | 0 |

TABLE 2-continued

| | | Application results | | | |
|---|---|---|---|---|---|
| | | Amount of Subjects with reactions | | | Subjects with reactions to uncomfortable |
| | cutaneous signs | T1 | T2 | T3 | sensation % |
| | Warm/Burning | 1 | 1 | 1 | 8 |
| | Discomfort | 0 | 0 | 0 | 0 |
| | Others | 0 | 0 | 0 | 0 |
| | Sum of felt sensation | 3 | 4 | 3 | 29 |
| Placebo | Tightness | 0 | 0 | 0 | 0 |
| | Stinging | 3 | 5 | 3 | 25 |
| | Itching/Pruritus | 1 | 3 | 1 | 13 |
| | Warm/Burning | 2 | 5 | 5 | 21 |
| | Discomfort | 0 | 0 | 0 | 0 |
| | Others | 2 | 0 | 0 | 8 |
| | Sum of felt sensation | 5 | 12 | 9 | 50 |

Under the mentioned study conditions it is obvious observed, that in comparison with the application of Placebo, when the sample comprising Frescolat MGA the amount of subjects having uncomfortable sensations at three evaluating time decreased respectively from 5 to 3, from 12 to 4, and from 9 to 3. In summary the percent of subjects with uncomfortable sensation decreased intensively from 50% to 29%.

The sample comprising Frescolat MGA according to the invention better relieved the subjects of the uncomfortable cutaneous signs compared to placebo.

Table 3 shows the intensity of the studied parameters at each assessment kinetic.

TABLE 3

| | | Intensity | | |
|---|---|---|---|---|
| | | Intensity of the sensation | | |
| | cutaneous signs | T1 | T2 | T3 |
| Sample | Tightness | 0.00 | 0.00 | 0.00 |
| | Stinging | 0.17 | 0.21 | 0.08 |
| | Itching/Pruritus | 0.00 | 0.00 | 0.00 |
| | Warm/Burning | 0.08 | 0.13 | 0.13 |
| | Discomfort | 0.00 | 0.00 | 0.00 |
| | Others | 0.00 | 0.00 | 0.00 |
| | Sum of felt sensation | 0.25 | 0.33 | 0.21 |
| Placebo | Tightness | 0.00 | 0.00 | 0.00 |
| | Stinging | 0.29 | 0.42 | 0.25 |
| | Itching/Pruritus | 0.13 | 0.29 | 0.13 |
| | Warm/Burning | 0.17 | 0.42 | 0.42 |
| | Discomfort | 0.00 | 0.00 | 0.00 |
| | Others | 0.17 | 0.08 | 0.00 |
| | Sum of felt sensation | 0.75 | 1.21 | 0.79 |

Intensity of sensation
0 = none
1 = very slight
2 = slight
3 = moderate
4 = severe Under these study conditions, it is obvious observed, that the sample comprising Frescolat MGA according to the invention presented a significant protective effect in comparison with the placebo: the felt intensity of the uncomfortable sensation (sum of stinging, burning and itching) at different time respectively from 0.75, 1.21 and 0.79 decreased to 0.25, 0.33 and 0.21.

Table 4 shows the evaluation by the hairdresser in comparison with placebo.

TABLE 4

Evaluation by hairdresser

| | Evaluated Criteria | Score |
|---|---|---|
| Sample | Shade Intensity | 9.5 |
| | Respect of attempted shade | 9.7 |
| Placebo | Shade Intensity | 9.0 |
| | Respect of attempted shade | 9.2 |

Shade Intensity
0 = none
10 = very slight
Respect of the attempted shade
0 = not at all
10 = exacted Under these study conditions, it is obvious observed, that the sample comprising Frescolat MGA according to the invention can not only relieve the uncomfortable sensation on the scalp, but also slight improved the colouring property of the hair colouring formulation. The results of the questionnaire were listed in Table 5:

TABLE 5

Product evaluation

| Evaluation of the tested product | % of subjects (agree/agree somewhat) | |
|---|---|---|
| | Sample | Placebo |
| calms, elimiates itching usually felt | 100 | 92 |
| Anti-burning | 96 | 83 |
| Reduces stinging | 96 | 84 |
| Reduces Itching | 100 | 88 |
| Removes tightness sensation | 100 | 100 |
| Refreshes the scalp | 96 | 83 |
| Soothes the scalp | 96 | 83 |
| Provides an immediate relief | 92 | 79 |
| A long-lasting anti-irritating effect | 100 | 83 |
| Diffuse an infinite relaxation | 91 | 92 |
| Increase the comfort of the scalp during the colouring | 92 | 92 |
| Increase the tolerance of the scalp | 96 | 88 |
| Appears to act as a protective shield | 100 | 91 |

From the listed results from the questionnaire it can be concluded, the by adding Frescolat MGA in the hair colouring formulation, its property has been improved the subjects prefer the effect realized by the formulation according to the invention.

In conclusion, the sample comprising Frescolat MGA according to the invention:

reduced the number of subjects with cutaneous signs compared to placebo (7 against 12);

presented a significant protective effect in comparison with the placebo;

presented a good intensity of the hair colouring and respected the attempted shade;

improved slightly the colouring property;

was appreciated by the subjects for its efficacy, for its soothing effect and for its properties/qualities.

The invention claimed is:

1. A method of permanent hair dyeing, comprising the following steps (i) mixing all the components of a composition consisting of:

(a) menthol compounds corresponding to formulas (I), (II) and/or (III)

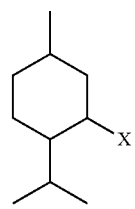

(I)

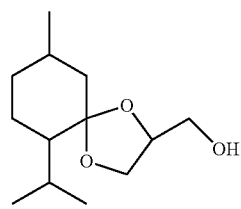

(II)

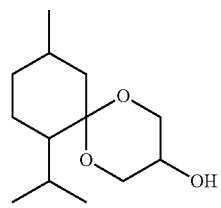

(III)

in which X represents —Y or —COZ and Y represents the following groups:

| (i) | a linear or branched alkyl or hydroxyl alkyl radical containing 1 to 6 carbon atoms or an allyl radical; |
|---|---|
| (ii) | a hydroxy or dihydroxyalkyl radical containing 1 to 6 carbon atoms; |
| (iii) | a radical —OCR$^1$; |
| (iv) | a radical —OCO(M)OH; |
| (v) | a radical —OCO—S; |
| (vi) | a radical —OC(CH$_2$)$_n$COR$^2$; | wherein

| M | represents a linear or branched alkyl and/or alkenyl radical containing 1 to 10, preferably, 1 to 4 carbon atoms; |
|---|---|
| S | represents a carbohydrate radical containing 5 to 12 carbon atoms, preferably, a fructose, a glucose or a sucrose radical; |
| n | stands for 0 or for numbers of 1 to 6, preferably, of 2 to 3; |
| R$^1$ | represents a linear or branched alkyl- or hydroxyl alkyl radical containing 1 to 6, preferably, 1 to 2 carbon atoms or an allyl radical; |
| R$^2$ | represents a hydroxyl radical or a radical —NR$^3$R$^4$; |
| R$^3$ | and R$^4$, independently of one another, represent hydrogen or a linear or branched alkyl or hydroxyl alkyl radical containing 1 to 6, preferably, 1 to 2 carbon atoms, | while Z represents the following groups:

| | |
|---|---|
| (vii) | a radical $NR^5R^6$, or |
| (viii) | a radical $NHR^7$, | wherein

| | |
|---|---|
| $R^5, R^6$ | independently of one another, represent hydrogen or a linear or branched alkyl or hydroxyl alkyl radical containing 1 to 6, preferably, 1 to 2 carbon atoms, a phenyl radical or an alkoxyphenyl radical containing 1 to 6, preferably, 1 to 2 carbon atoms in the alkoxy radical; |
| $R^5, R^6, R^7$ | represent a radical —$(CH_2)_n COOR^8$; |
| $R^8$ | represents a linear or branched alkyl or hydroxy alkyl radical containing 1 to 6, preferably, 1 to 2 carbon atoms, and |
| n | stands for 0 or for numbers of 1 to 10, preferably, of 1 to 4, and |

(b) a cosmetically acceptable carrier, and
(c) a hair colouring formulation and/or a hair straightening formulation having a pH of from 6.5 to 12; and consisting of
  (c-1) at least one separately provided oxidizing agent, and
  (c-2) at least one oxidation base, and
  (c-3) at least one synthetic dye, and/or
  (c-4) at least one natural dye,
wherein the composition is in the absence of menthofuran, and applying the obtained mixture onto the hair of a person having a sensitive scalp:
  (ii) leaving the mixture of step (i) on the hair for a defined time; then
  (iii) rinsing the hair.

2. The method of claim 1 wherein the menthol compounds are present in the composition in an amount from 5 t 65 wt. %.

3. The method of claim 1, wherein the menthol compounds are selected from the group consisting of menthone glycerine acetal, menthone glycerine ketal and mixtures thereof.

* * * * *